United States Patent
Magee

(10) Patent No.: US 8,439,887 B1
(45) Date of Patent: May 14, 2013

(54) REUSABLE ADJUSTABLE DIAPER

(76) Inventor: Stacee M. Magee, Mesa, AZ (US)

( * ) Notice: Subject to any disclaimer, the term of this patent is extended or adjusted under 35 U.S.C. 154(b) by 302 days.

(21) Appl. No.: 13/050,795

(22) Filed: Mar. 17, 2011

Related U.S. Application Data

(62) Division of application No. 12/008,331, filed on Jan. 10, 2008, now Pat. No. 7,914,507.

(60) Provisional application No. 60/912,691, filed on Apr. 19, 2007.

(51) Int. Cl.
*A61F 13/15* (2006.01)
*A61F 13/20* (2006.01)

(52) U.S. Cl.
USPC ............ 604/385.01; 604/385.14; 604/385.15; 604/385.16; 604/385.25; 604/385.26; 604/385.27; 604/385.28; 604/399

(58) Field of Classification Search ............. 604/385.01, 604/385.14–385.16, 385.25–385.28, 399
See application file for complete search history.

(56) References Cited

U.S. PATENT DOCUMENTS

| | | | |
|---|---|---|---|
| 2,347,867 A | 5/1944 | Alban | |
| 2,620,798 A | 12/1952 | O'Brien | |
| 2,703,577 A | 3/1955 | May | |
| 2,815,026 A | 12/1957 | Meyer | |
| 3,162,196 A | 12/1964 | Salk | |
| 3,566,870 A | 3/1971 | Benjamin | |
| 4,397,646 A | 8/1983 | Daniels et al. | |
| 4,548,604 A | 10/1985 | Ellsworth | |
| 4,834,739 A | 5/1989 | Linker, III et al. | |
| 4,981,480 A | 1/1991 | Gaudet et al. | |
| 5,019,068 A | 5/1991 | Perez | |
| 5,451,219 A | 9/1995 | Suzuki | |
| 5,814,037 A | 9/1998 | Coates | |
| 6,394,988 B1 | 5/2002 | Hashimoto | |
| 6,406,469 B1 | 6/2002 | Brain | |
| 6,579,273 B2 | 6/2003 | Dupuy | |
| 6,616,645 B1 | 9/2003 | Moravek | |
| 6,817,992 B1 | 11/2004 | Sassak | |
| D610,255 S | 2/2010 | Garner | |
| 2002/0010452 A1 | 1/2002 | Dupuy | |
| 2008/0065039 A1 | 3/2008 | Labit et al. | |
| 2008/0195075 A1 | 8/2008 | Ruocco | |

OTHER PUBLICATIONS

"Bum Genius" web page Downloaded Dec. 4, 2007, http:/www.wonderoos.com/information.htm.
"Wonderoos" web page Downloaded Dec. 4, 2007, http:/www.wonderoos.com/information.htm.
"Mommy's Touch" web page Downloaded Dec. 4, 2007, http:/www.mommystouch.com/fitted.html.
"Cuddle Buns" web page Downloaded Dec. 4, 2007, http:/www.cuddlebunsdiapers.com/products.htm.
http:/www.zany-zebra.com/diaper-fabric.shtml.

*Primary Examiner* — Tatyana Zalukaeva
*Assistant Examiner* — Ginger T Chapman
(74) *Attorney, Agent, or Firm* — Desandro Law Group PLLC; Bradley K. DeSandro

(57) ABSTRACT

The invention, a reusable adjustable diaper, includes: a multi-ply member having a first curvilinear portion connecting by a medial portion to a second curvilinear portion; a first elastomeric member connected to a first curved segment of multi-ply member and having a first plurality of fastening areas; a second elastomeric member connected to a second curved segment of multi-ply member and having a second plurality of fastening areas; a first plurality of fasteners connected to first curvilinear portion; a second plurality of fasteners connected to second curvilinear portion and disengagably fastenable with first plurality of fasteners; a third fastener connected to multi-ply member and disengagably fastenable with first elastomeric member at each of first plurality of fastening areas; and a fourth fastener connected to multi-ply member and disengagably fastenable with second elastomeric member at each of second plurality of fastening areas.

20 Claims, 10 Drawing Sheets

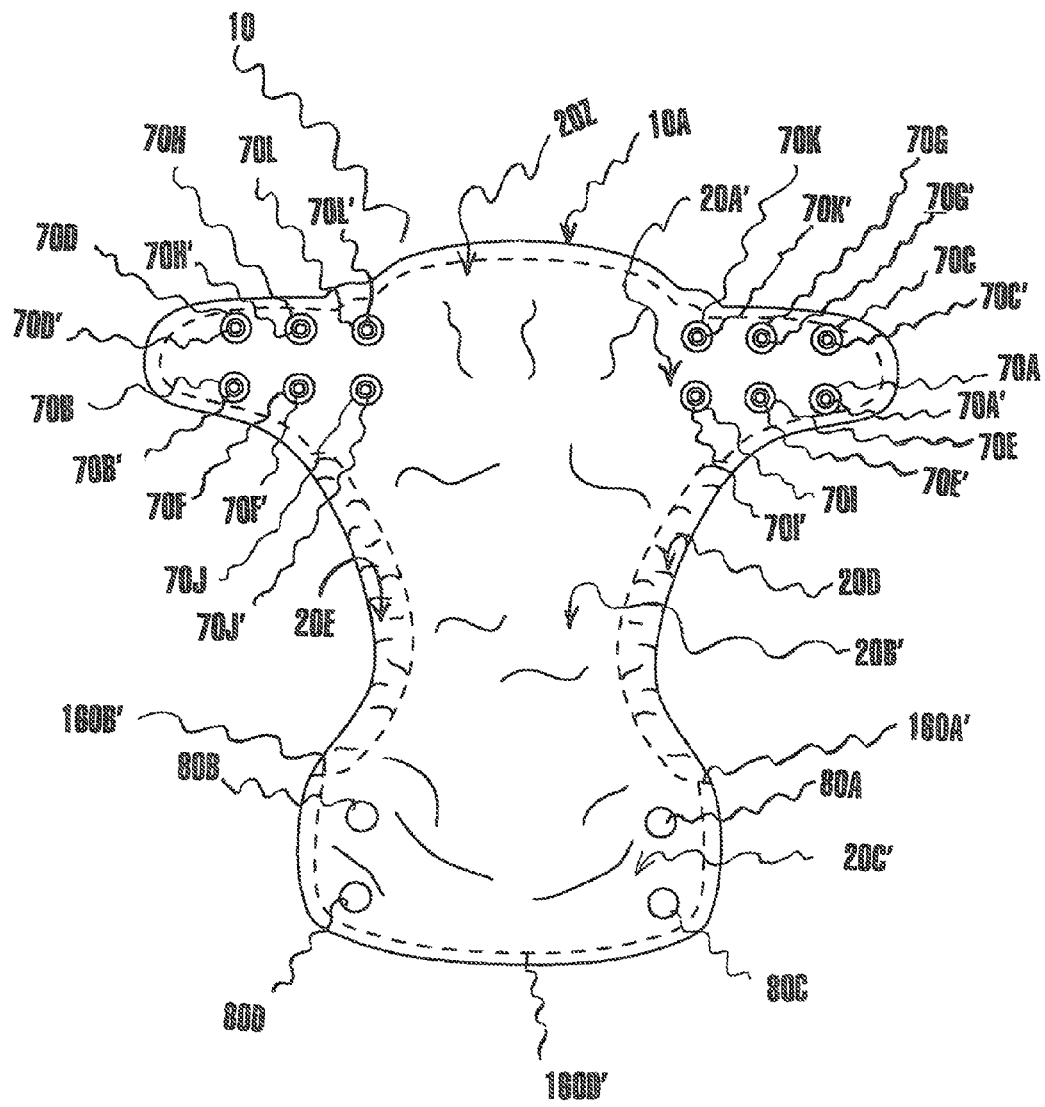

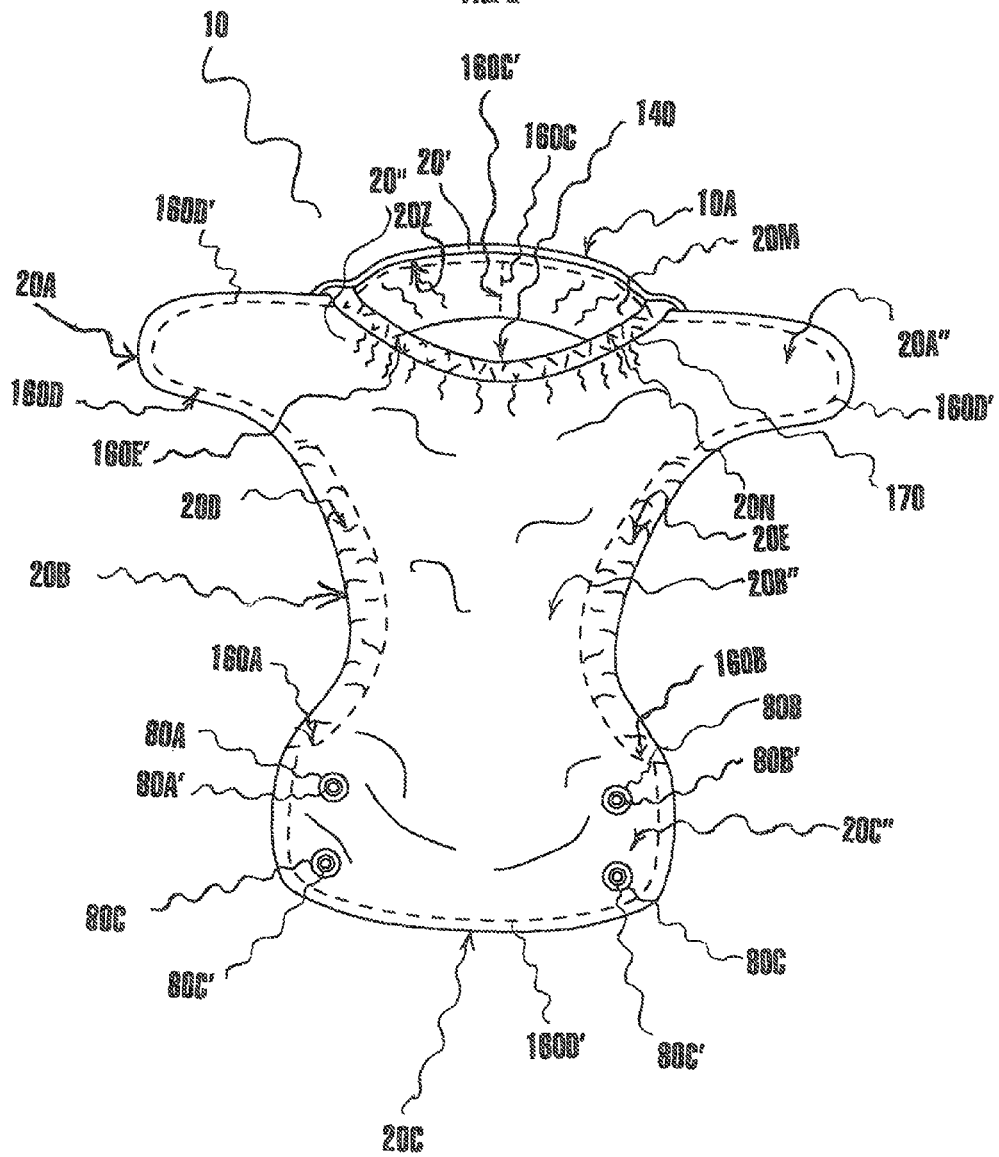

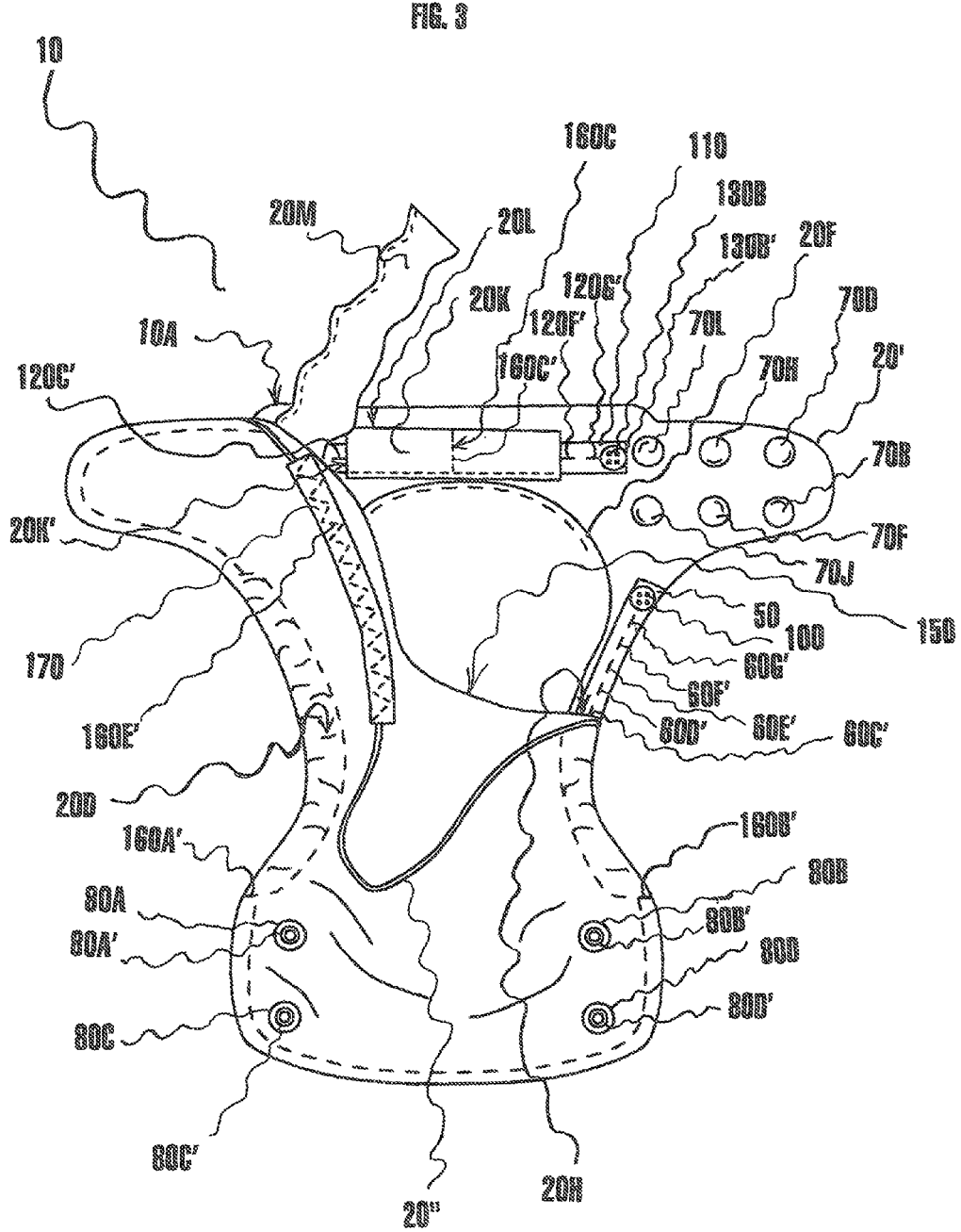

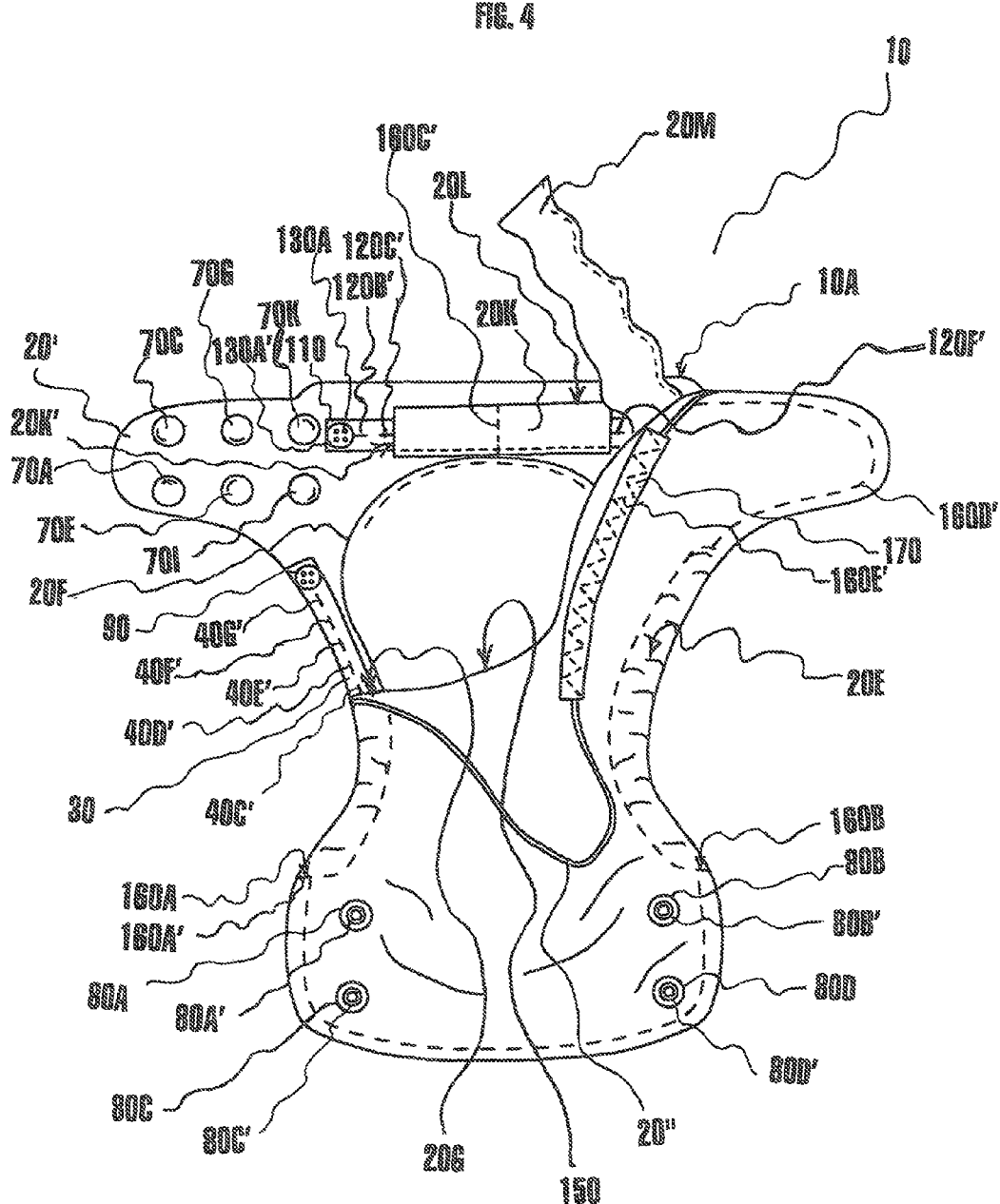

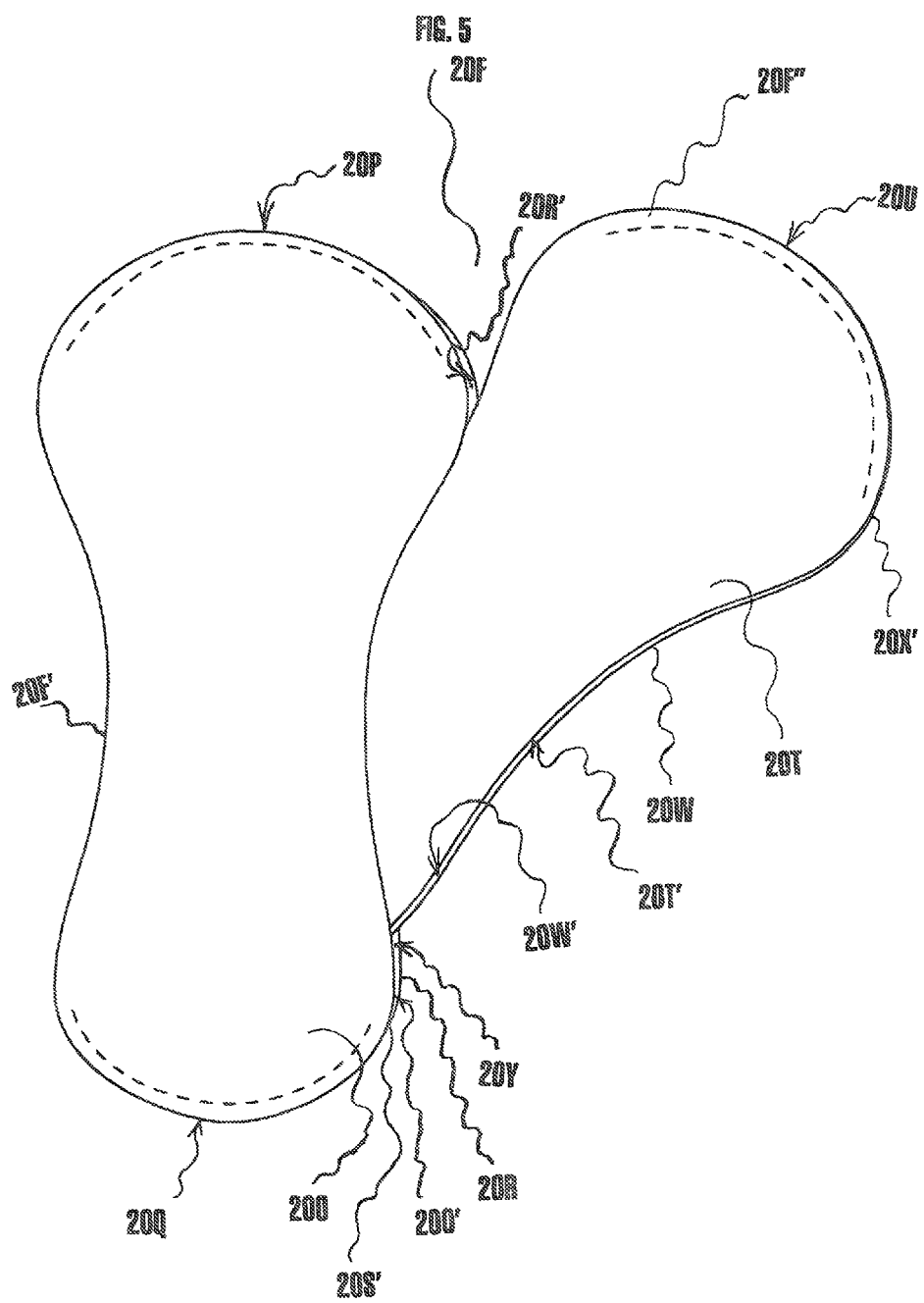

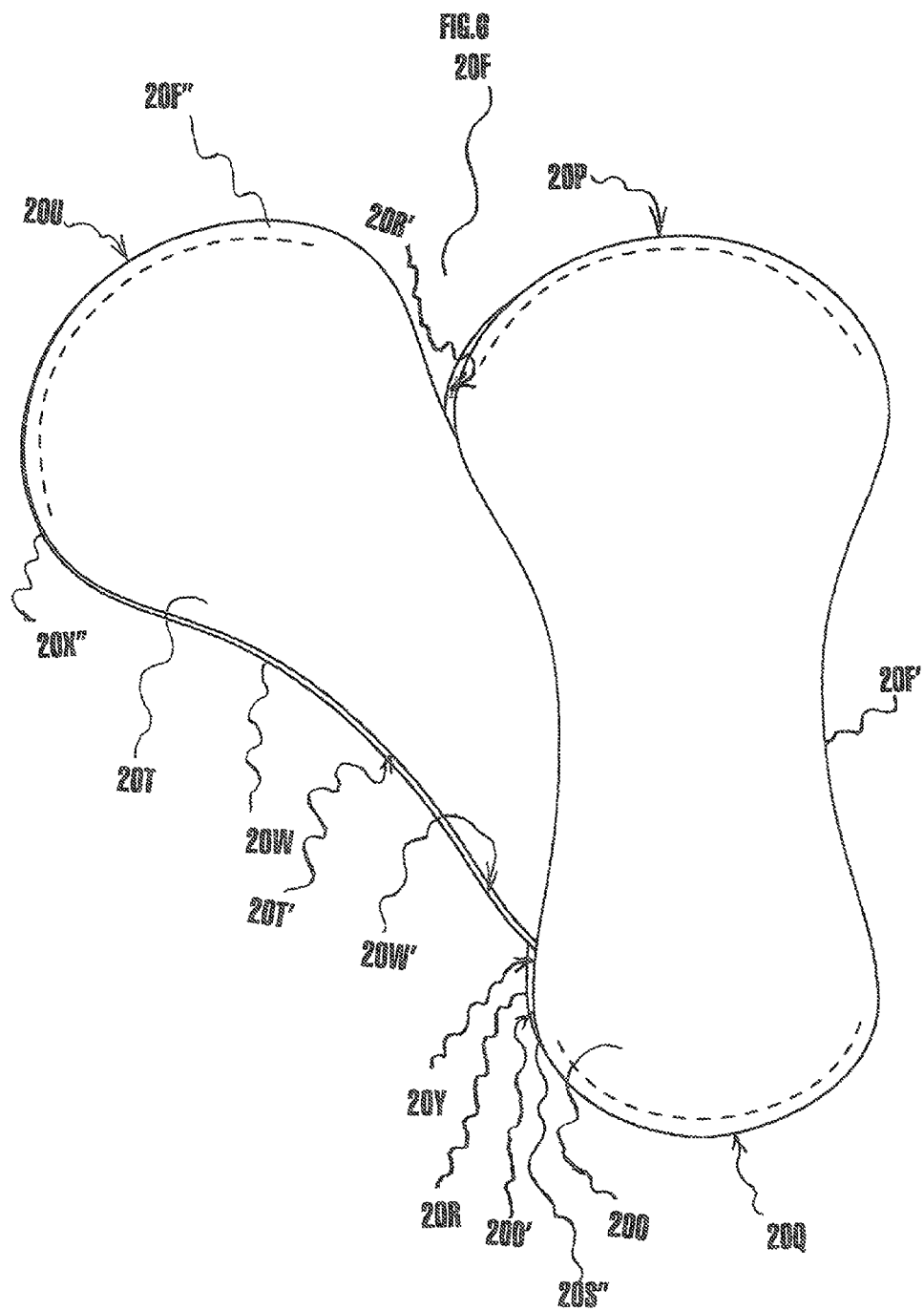

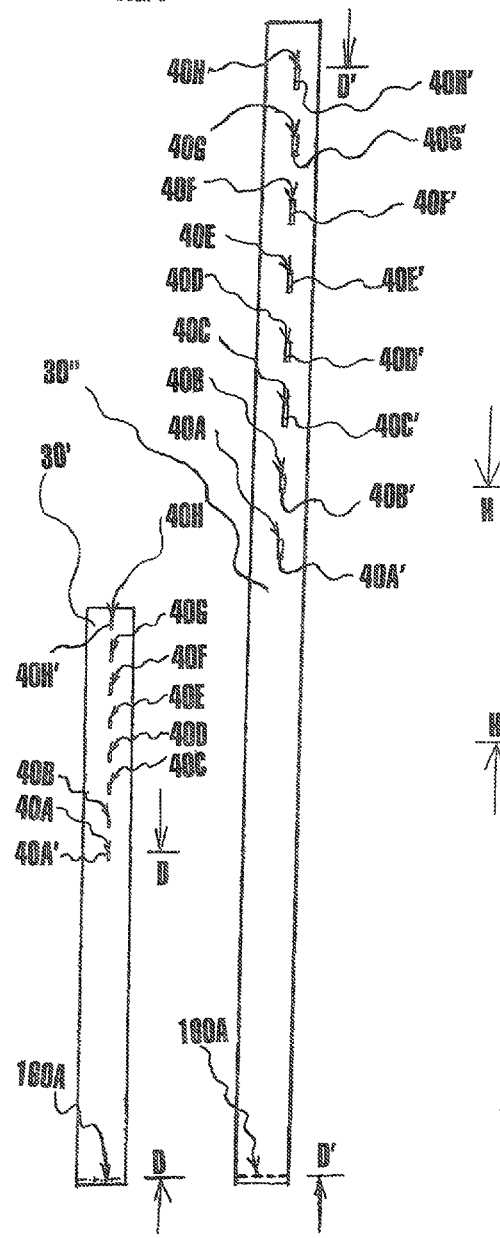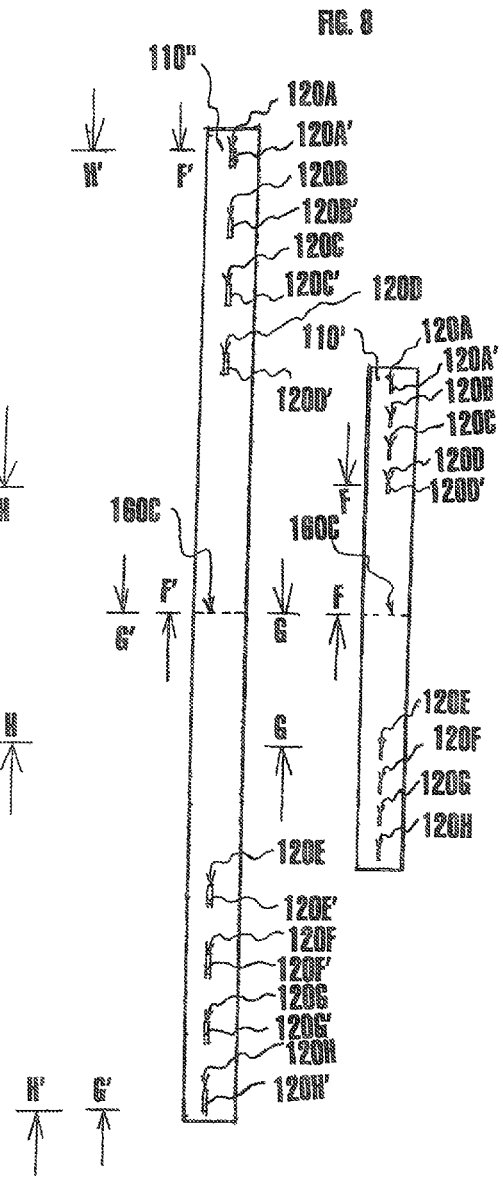

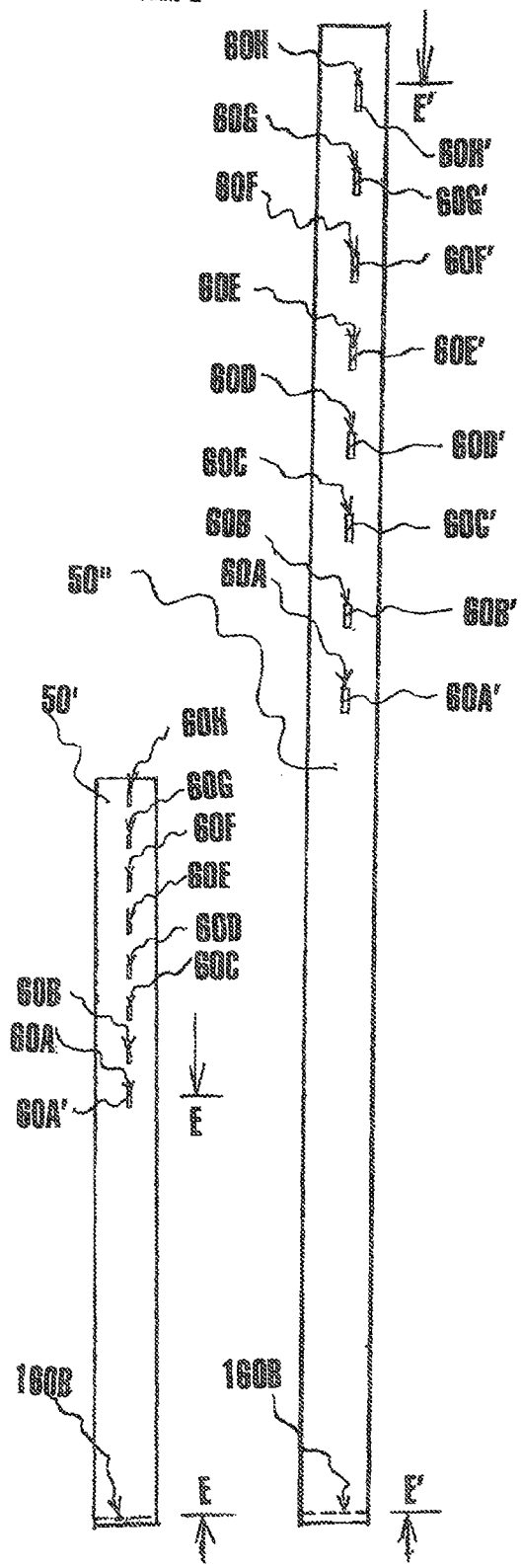

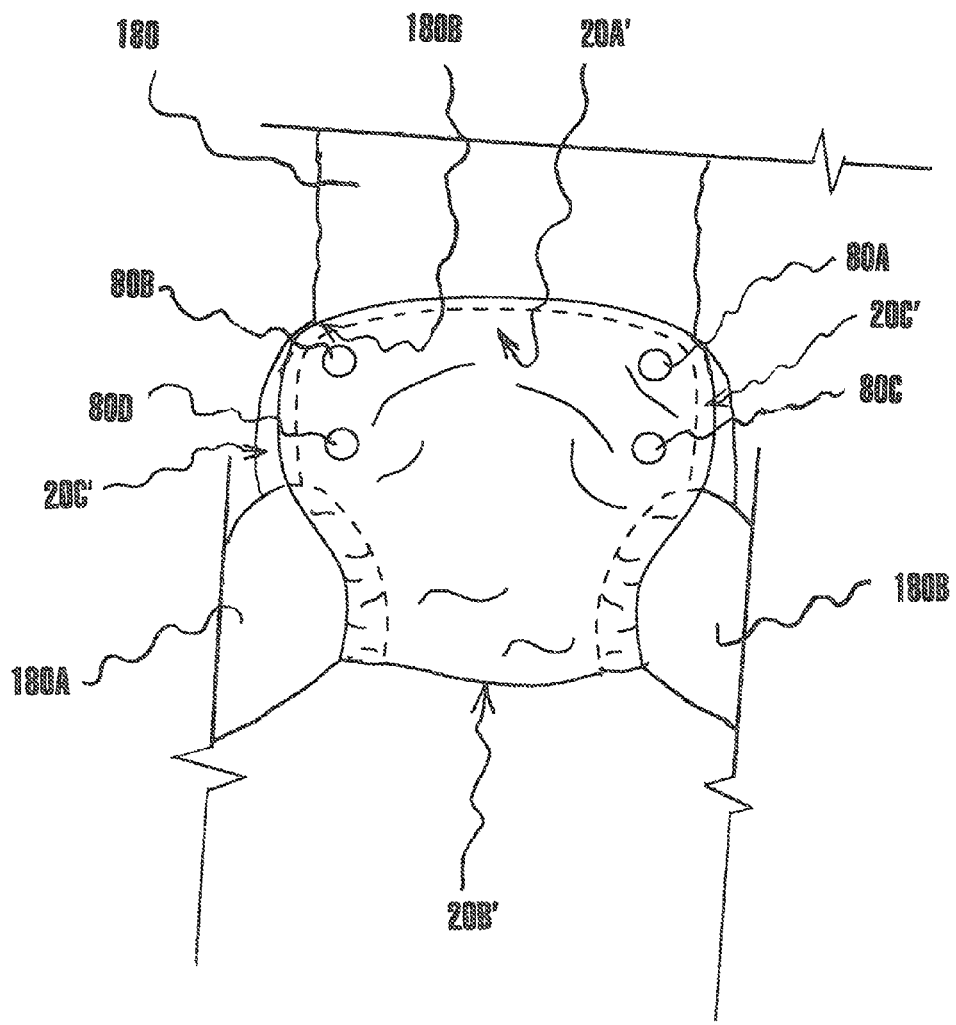

REUSABLE ADJUSTABLE DIAPER

CROSS REFERENCE TO RELATED APPLICATIONS

This application is a divisional of U.S. patent application entitled "REUSABLE ADJUSTABLE DIAPER," Ser. No. 12/008,331, filed Jan. 10, 2008, which claims priority to Provisional Patent Application No. 60/912,691 entitled "Adjustable Diaper" filed Apr. 19, 2007, the disclosures of which are incorporated entirely herein by reference.

TECHNICAL FIELD

This invention relates a reusable adjustable diaper. More specifically, this invention relates to a reusable adjustable diaper that is easily assembled, cleaned and adjustable to accommodate differing sizes and waste capture needs of individual diaper wearers.

BACKGROUND OF THE INVENTION

The present invention addresses problems encountered in providing a reusable diaper for capturing waste expelled from a diaper wearer's anus and urogenital systems which is easily assembled, cleaned and adjustable to accommodate wearers of differing sizes with differing waste capture requirements.

While a variety of diapering devices are known, a significant portion are used only a single time before being discarded. Many are composed in whole or in part of polymers or other synthetics that are either expensive to produce or may take long periods to degrade after disposal. Among diapering devices that are reusable, some are not easily cleaned. Some require that "plastic pants" or another separate liquid impermeable liner be worn outside the diaper to contain waste that may seep through the diaper. Most reusable diapers are not easily modifiable to comfortably and securely accommodate a growing diaper wearer or a diaper wearer having different sized legs. Yet further, most do not provide an easily reusable assembly for selectively modifying the absorbency and weight of the diaper to meet the varying waste capture, weight and size needs of individual diaper wearers.

The present invention addresses the foregoing problems and provides a durable, comfortable, reusable adjustable diaper for capturing waste expelled from a diaper wearer's anus and urogenital systems which is easily assembled, cleaned and adjustable for diaper wearers of differing sizes and with differing waste capture needs. While various devices in the prior art disclose some of the general structural and operational features of the instant invention, no device in the known prior art includes the overall structure and functional features of the present invention.

Among other distinguishing functional characteristics of the present invention are: (1) the present invention's distinctive leg engaging elastomeric members, each having a particularly sized, shaped, spaced and oriented plurality of fastening areas disengagably fastenable with an associated fastener; (2) the present invention's distinctive waist-engaging elastomeric member with its particularly sized, shaped, spaced and oriented plurality of fastening areas, each fastening area being disengagably fastenable with an associated additional plurality of fasteners; (3) the present invention's distinctive and selectively absorbent reusable pad assembly that is easily inserted through a distinctively shaped and oriented incurvate opening into a cavity between an inner ply and an outer ply of the present invention's reusable adjustable diaper to facilitate selectively adjustable waste capture and the easy removal, washing and drying of the pad assembly after use.

The overall structural and functional features of the present invention promote efficiency, simplicity and ease of operation and allow the present invention to: (1) provide a distinctively adjustable, snug, secure, waste-retaining fit around an unlimited number of differing first leg and second leg sizes of a diaper wearer; (2) provide such distinctively adjustable, snug, secure fit without need of a leg-encircling elastic or leg encircling band; (3) provide a distinctively adjustable, snug, secure, waste-retaining fit around an unlimited number of waist sizes of a diaper wearer; (4) provide such distinctively adjustable, snug, secure fit without need of a waist-encircling elastic or band; and (5) provide a reusable pad assembly of selective absorbency which is conveniently inserted into a cavity formed between an inner ply and outer ply of the reusable adjustable diaper of the present invention and which is easily and rapidly removed, washed and dried after diaper usage.

SUMMARY OF THE INVENTION

It is an object of this invention to provide a reusable adjustable diaper. More specifically, it is an object of this invention to provide a reusable adjustable diaper that is easily assembled, cleaned and adjustable to accommodate differing sizes and waste capture needs of individual diaper wearers. The reusable adjustable diaper includes: (1) a multi-ply member having a first curvilinear portion connected by a narrowing curved medial portion to a second curvilinear portion; (2) a first elastomeric member operatively connected along a first curved segment of the medial portion, the first elastomeric member having a first plurality of fastening areas disposed therewith, (3) a second elastomeric member operatively connected along a second curved segment of the medial portion, the second elastomeric member having a second plurality of fastening areas disposed therewith; (4) a first plurality of fasteners operatively connected to the first curvilinear portion; (5) a second plurality of fasteners operatively connected to the second curvilinear portion and being disengagably fastenable with the first plurality of fasteners to adjustably secure the diaper in a wearing orientation; (6) a third fastener operatively connected to the multi-ply member and being disengagably fastenable with the first elastomeric member at the first plurality of fastening areas; and (7) a fourth fastener operatively connected to the multi-ply member and being disengagably fastenable with the second elastomeric member at the second plurality of fastening areas. An embodiment of the reusable adjustable diaper may further include: a third elastomeric member operatively connected to the first curvilinear portion and having a third plurality of fastening areas disposed therewith, and a fifth plurality of fasteners operatively connected to the first curvilinear portion and being disengageably fastenable with the third elastomeric member at the third plurality of fastening areas.

Another object of this invention is to provide a reusable adjustable diaper in accordance with the foregoing paragraph that is easily, efficiently and sanitarily assembled, used and then disassembled and cleaned for reuse.

Another object of this invention is to provide a reusable adjustable diaper in accordance with the previous two paragraphs that allows an easily adjustable, comfortable waste-retaining fit around an unlimited number of differing first leg and second leg sizes of a diaper wearer without need of a leg-encircling elastic or band for either such leg.

Another object of a preferred embodiment of this invention is to provide a reusable adjustable diaper in accordance with the previous three paragraphs that allows an easily adjustable, comfortable waste-retaining fit around an unlimited number of differing waist sizes of a diaper wearer without need of a waist encircling elastic or band.

Another object of this invention is to provide a reusable adjustable diaper in accordance with the preceding objects that includes a reusable pad assembly of selective absorbency which is conveniently inserted and selectively retained between an inner ply and an outer ply of the reusable adjustable diaper of the present invention and which is easily and rapidly removed, washed and dried after diaper usage.

Another object of a preferred embodiment of this invention is to provide a reusable adjustable diaper in accordance with the preceding objects which requires no "plastic pants" or other additional liquid impermeable liner to be worn outside the diaper to contain waste.

Another object of the invention is to provide a reusable adjustable diaper assembly with the stability, ease and simplicity of an invention having a minimum number of component parts to accomplish the preceding objects.

Another object of this invention is to provide a durable reusable adjustable diaper in accordance with the preceding objects which will conform to conventional forms of manufacture, be of comparatively simple construction and easy to use so as to provide an assembly that will be economically feasible, durable and relatively free of trouble in use and operation.

These together with the other objects and advantages of the invention which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a bottom plan view of an embodiment of the reusable adjustable diaper of the present invention.

FIG. 2 is a top plan view of an embodiment of the reusable adjustable diaper of the present invention.

FIG. 3 is top plan view of an embodiment of the reusable adjustable diaper of the present invention with a portion of an inner ply peeled away from the remainder of the diaper.

FIG. 4 is top plan view of an embodiment of the reusable adjustable diaper of the present invention with a second portion of an inner ply peeled away from the remainder of the diaper.

FIG. 5 is a perspective view of an embodiment of a reusable pad assembly of the reusable adjustable diaper of the present invention.

FIG. 6 is a second perspective view of an embodiment of a reusable pad assembly of the reusable adjustable diaper of the present invention.

FIG. 7 is a plan view of an embodiment of a first elastomeric member of the present invention shown in alternate constricted and fully expanded configurations, the first elastomeric member having a first plurality of fastening areas.

FIG. 8 is a plan view of an embodiment of a third elastomeric member of the present invention shown in alternate constricted and fully expanded configurations, the third elastomeric member having a third plurality of fastening areas.

FIG. 9 is a plan view of an embodiment of a second elastomeric member of the present invention shown in alternate constricted and fully expanded configurations, the second elastomeric member having a first plurality of fastening areas.

FIG. 11 is a front plan view of an embodiment of the reusable adjustable diaper of the present invention shown in operative connection with a diaper wearer's legs and waist.

DETAILED DESCRIPTION OF INVENTION

Figure 10:
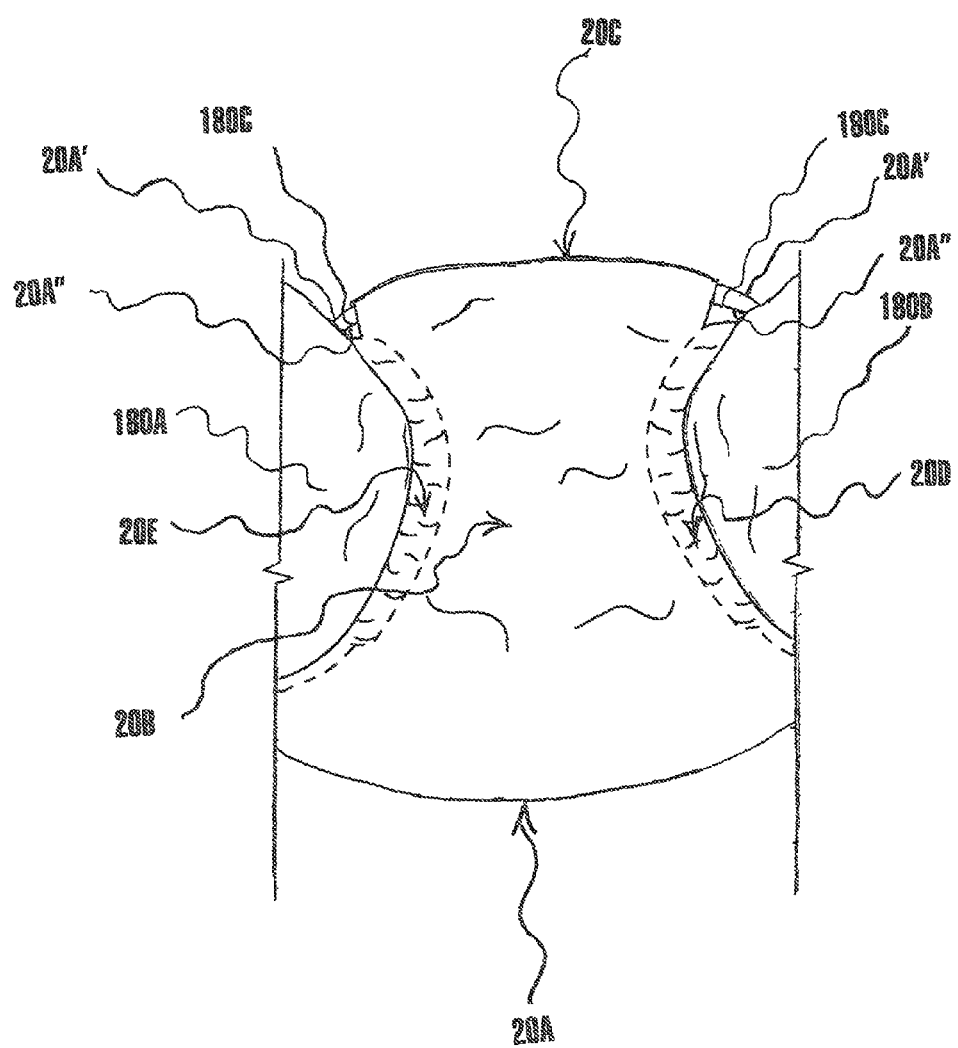
FIG. 10 is a partial bottom plan view of an embodiment of the reusable adjustable diaper of the present invention in operative connection with a diaper wearer's legs and waist.

FIGS. 1 through 4 illustrate a preferred embodiment of a reusable adjustable diaper 10. In standard operation, the diaper is adjustably fitted to snugly and comfortably engage about the legs of a human wearer and serves to capture and contain fecal material, urine and other waste expelled from the wearer's anus and urogenital systems thus preventing accidents and unwanted mess without need of a disposable diaper.

With attention directed principally to FIGS. 1 through 4 it is seen that a preferred embodiment of the diaper 10 includes: (1) a multi-ply member 20 having a first curvilinear portion 20A operatively connected by a narrowing curved medial portion 20B to a second curvilinear portion 20C; (2) a first elastomeric member 30 (FIG. 4) operatively connected along a first curved segment 20D of the medial portion 20C, the first elastomeric member 30 having a first plurality of fastening areas 40A, 40B, 40C, 40D, 40E, 40F, 40G, 40H disposed therewith, the first elastomeric member 30 being resiliently stretchable between a constricted configuration 30' (FIG. 7) and a fully expanded configuration 30" (FIG. 7); (3) a second elastomeric member 50 operatively connected along a second curved segment 20E of the medial portion 20C, the second elastomeric member 50 (FIG. 3) having a second plurality of fastening areas 60A, 60B, 60C, 60D, 60E, 60F, 60G, 60R disposed therewith, the second elastomeric member 50 being resiliently stretchable between a constricted configuration 50' (FIG. 9) and a fully expanded configuration 50" (FIG. 9); (4) a first plurality of fasteners 70A, 70B, 70C, 70D, 70E, 70F, 70G, 70R, 70I, 70J, 70K, 70L (FIG. 1) operatively connected to the first curvilinear portion 20A; (5) a second plurality of fasteners 80A, 80B, 80C, SOD (FIG. 1) operatively connected to the second curvilinear portion 20C and cooperatively and disengagably fastenable with the first plurality of fasteners 70A, 70B, 70C, 70D, 70E, 70F, 70G, 70R, 70I, 70J, 70K, 70L to configure the diaper in alternative wearing and cleaning orientations, a wearing orientation being seen generally seen in FIGS. 10 and 11 and a cleaning orientation being seen in FIGS. 1 and 2; (6) a third fastener 90 (FIG. 4) operatively connected to the multi-ply member 20 and being disengagably fastenable with the first elastomeric member 30 at the first plurality of fastening areas 40A, 40B, 40C, 40D, 40E, 40F, 40G, 40R; and (7) a fourth fastener 100 (FIG. 3) operatively connected to the multi-ply member 20 and disengagably fastenable with the second elastomeric member 50 at the second plurality of fastening areas 60A, 60B, 60C, 60D, 60E, 60F, 60G, 60R. In a preferred embodiment, the first plurality of fasteners 70A, 70B, 70C, 70D, 70E, 70F, 70G, 70R, 70I, 70J, 70K, 70L and the second plurality of fasteners 80A, 80B, 80C, 80D include mateable snap assemblies, each mateable snap assembly having a female portion 70A', 70B', 70C' 70D', 70E', 70F', 70G', 70H', 70I', 70J', 70K', 70L' (FIG. 1) and a male portion SOA', SOB', SOC' SOD' (FIGS. 2, 3 and 4) insertable in the female portion.

With attention further directed primarily to FIGS. 3 and 4, a preferred embodiment of the diaper 10 also includes: (1) a third elastomeric member 110 operatively connected to the first curvilinear portion 20A along an upper segment 20L of the first curvilinear portion, the third elastomeric member 110 having a third plurality of fastening areas 120A, 120B, 120C, 120D, 120E, 120F, 120G, 120H disposed therewith, and the third elastomeric member 110 being resiliently stretchable between a constricted configuration 110' (FIG. 8) and a fully expanded configuration 110" (FIG. 8); and (2) a fifth plurality of fasteners 130A, 130B operatively connected to the first curvilinear portion 20A and cooperatively and disengageably fastenable with the third elastomeric member 110 at the third plurality of fastening areas 120A, 120B, 120C, 120D, 120E, 120F, 120G, 120H.

Referring further to FIGS. 3 and 4, it is seen that a preferred embodiment of the multi-ply member 20 includes: (1) an outer ply 20' having a first outer ply curvilinear portion 20A' connected by a narrowing curved outer ply medial portion 20B' to an outer ply second curvilinear portion 20C'; and (2) an inner ply 20" having a first inner ply curvilinear portion 20A" connected by a narrowing curved inner ply medial portion 20B" to an inner ply second curvilinear portion 20C", the inner ply 20" being operatively connected to the outer ply 20' most preferably by a fourth plurality of thread segments 160D' stitched through the outer ply 20' and the inner ply 20" at a peripherally located fourth permanent connection area 160D. A reusable pad assembly 20F is removably inserted through an insertion aperture 140 into a cavity 150 formed between the outer ply 20' and the inner ply 20". As perhaps best seen in FIG. 2, the insertion aperture 140 is not formed on a leading edge 10A of the diaper 10 and the multi-ply member 20 but is instead preferably formed at an incurvate opening area 20N medially disposed to the leading edge 10A allowing a grip tab area 20Z of the multi-ply member 20 to be formed and disposed peripherally to the incurvate opening area 20N. In an embodiment of the diaper 10, a fourth elastomeric member 170 (FIGS. 2, 3 and 4) is operatively connected to the inner ply 20" most preferably by a fifth thread segment 160E' stitched through the inner ply 20" and the fourth elastomeric member 170. The fourth elastomeric member 170 functions inter alia to facilitate easy insertion and secure retention of the reusable pad assembly, to protect and make the inner ply 20" more durable and to promote a snug, comfortable waste-retaining fit of the inner ply 20" with the diaper wearer.

The inner ply 20" is preferably composed of a wicking fabric, which comfortably draws wetness away from a diaper wearer 180. The outer ply 20' is preferably composed of water impermeable material, most preferably a breathable or non-breathable polyurethane laminate and assists in preventing fecal material, urine and other waste expelled from the wearer's anus and urogenital systems from escaping and in preventing unwanted unconfined mess. The reusable pad assembly 20F (FIGS. 3 and 4) is composed of a water absorbing material and preferably includes: (1) a jacket 20F' (FIGS. 5 and 6) and (2) an insert 20F" (FIGS. 5 and 6).

Referring principally to FIGS. 4 and 6 it is seen that: (1) a first elastomeric member 30 is disposed along a first curved segment 20D of the medial portion 20B and has a first plurality of fastening areas 40A, 40B, 40C, 40D, 40E, 40F, 40G, 40H disposed therewith, and (2) the third fastener 90 is operatively connected to the multi-ply member 20 and is disengagably fastenable with the first elastomeric member 30 at the first plurality of fastening areas 40A, 40B, 40C, 40D, 40E, 40F, 40G, 40H. In a preferred embodiment, the first plurality of fastening areas 40A, 40B, 40C, 40D, 40E, 40F, 40G, 40H are formed by a first plurality of uniformly sized and spaced apart apertures 40A', 40B', 40C', 40D', 40E', 40F', 40G', 40H' disposed through the first elastomeric member 30 and the third fastener 90 includes a first button 90' that is selectively and disengageably fastenable with the first elastomeric member 30 through apertures among the first plurality of apertures 40A', 40B', 40C', 40D', 40E', 40F', 40G', 40H'. It is, however, to be appreciated that a fastening area can alternatively be positioned at any area where the first elastomeric member 30 is adapted to be selectively and disengageably fastenenable with any third fastener 90 and that the first plurality fastening areas 40A, 40B, 40C, 40D, 40E, 40F, 40G, 40H and third fastener 90 may alternatively be formed by other selectively mateable fastening assemblies including, without limitation, mateable hooks and piles, mateable hooks and latches or mateable hooks and loops. In a preferred embodiment best seen in FIG. 4, the first elastomeric member 30 operatively connects to the multi-ply member 20 through a first channel 20G disposed along a first curved segment 20D of the medial portion 20B of the multi-ply member 20 and is permanently connected to the multi-ply member 20 at a first permanent connection area 160A by a first thread segment 160A' stitched through the first elastomeric member 30 and the multi-ply member 20. The features in this paragraph function to provide a reusable adjustable diaper 10 to form a comfortable yet snug, secure, waste-retaining fit around an unlimited number of differing first leg sizes of the diaper wearer including any first leg 180A size with a circumference: (1) equal to or greater than a first minimum distance D (FIG. 7) from the first permanent connection area 160A to a fastening area among the first plurality of fastening areas 40A, 40B, 40C, 40D, 40E, 40F, 40G, 40H most proximate the first permanent connection area 160A when the first elastomeric member 30 is in a constricted configuration 30' (FIG. 7) and (2) equal to or less than a first maximum distance D' (FIG. 7) between the first permanent connection area 160A and an additional fastening area among the first plurality of fastening areas 40A, 40B, 40C, 40D, 40E, 40F, 40G, 40H most distal the first permanent connection area 160A when the first elastomeric member 30 is in a fully expanded configuration 30" (FIG. 7).

Referring primarily to FIGS. 3 and 8 it is seen that: (1) a second elastomeric member 50 is disposed along a second curved segment 20E of the medial portion 20B and has a second plurality of fastening areas 60A, 60B, 60C, 60D, 60E, 60F, 60G, 60H disposed therewith and (2) a fourth fastener 100 is operatively connected to the multi-ply member 20 and is disengagably fastenable with the second member 50 at the second plurality of fastening areas 60A, 60B, 60C, 60D, 60E, 60F, 60G, 60H. In a preferred embodiment, the second plurality of fastening areas 60A, 60B, 60C, 60D, 60E, 60F, 60G, 60H are formed by a second plurality of uniformly sized and spaced apart apertures 60A', 60B', 60C', 60D', 60E', 60F', 60G', 60H' disposed through the second elastomeric member 50 and the fourth fastener 100 includes a second button 100' operatively connected to the multi-ply member 20 that is selectively and disengageably fastenable with the second elastomeric member 50 through the apertures 60A', 60B', 60C', 60D', 60E', 60F', 60G', 60H'; it is, however, to be appreciated that a fastening area can alternatively be positioned at any area where the second elastomeric member 50 is adapted to be selectively and disengageably fastenenable with any fourth faster 100 and that the second plurality of fastening areas 60A, 60B, 60C, 60D, 60E, 60F, 60G, 60H and fourth fastener 100 may alternatively be formed by other selectively mateable fastening assemblies including, without limitation, mateable hooks and piles, mateable hooks and latches and mateable hooks and loops. In a preferred embodiment, the second elastomeric member 50 is operatively connected to the multi-ply member 20 by a second channel 20H disposed along a second curved segment 20E of the medial portion 20B of the multi-ply member 20 and is permanently secured to the multi-ply member 20 at a second permanent connection area 160B preferably by a second thread segment 160B' stitched through the second elastomeric member 50 and the multi-ply member 20. The features described in this paragraph function inter alia to provide a reusable adjustable diaper 10 to form a comfortable yet snug, secure, waste-retaining fit around an unlimited number of differing second leg 180B sizes of the diaper wearer including any second leg size with a circumference: (1) equal to or greater than a second minimum distance E (FIG. 9) from the second permanent connection area 160B to a fastening area among the second plurality of fastening areas 60A, 60B, 60C, 60D, 60E, 60F, 60G, 60H most proximate the second permanent connection area 160B when the second elastomeric member 50 is in a constricted configuration 50' (FIG. 9) and (2) equal to or less than a second maximum distance E' (FIG. 9) between the second permanent connection area 160B and a second fastening area among the second plurality of fastening areas 60A, 60B, 60C, 60D, 60E, 60F, 60G, 60H most distal the second permanent connection area 160B when the second elastomeric member 50 is in a fully expanded configuration 50" (FIG. 9). Moreover, the features described in this paragraph function independently of those in the preceding paragraph and accordingly provide a reusable adjustable diaper 10 that not only forms a comfortable yet snug, secure, waste-retaining fit around the legs of different sized diaper wearers but also the formation of such a fit simultaneously around two differently sized legs 180A, 180B (FIGS. 10 and 11) of the same diaper wearer.

With attention directed principally to FIGS. 3, 4 and 8 it is further seen that a preferred embodiment of the diaper 10 also includes: (1) a third elastomeric member 110 operatively connected to the first curvilinear portion 20A proximate an upper segment 20L of the first curvilinear portion, the third elastomeric member 110 having a third plurality of fastening areas 120A, 120B, 120C, 120D, 120E, 120F, 120G, 120H disposed therewith; and (2) a fifth plurality of fasteners 130A, 130B operatively connected to the first curvilinear portion 20A and cooperatively and disengageably fastenable with the third elastomeric member 110 at the third plurality of fastening areas 120A, 120B, 120C, 120D, 120E, 120F, 120G, 120H. In a preferred embodiment: a) the third plurality of fastening areas 120A, 120B, 120C, 120D, 120E, 120F, 120G, 120H includes a first sub-plurality of fastening areas 120A, 120B, 120C, 120D formed by a first sub-plurality of uniformly sized and spaced apart apertures 120A', 120W, 120C', 120D' disposed through the third elastomeric member 110 and a second sub-plurality of fastening areas 120E, 120F, 120G, 120H formed by a second sub-plurality of uniformly sized and spaced apart apertures 120E', 120F' 120G', 120H' disposed through the third elastomeric member 110; and b) the fifth plurality of fasteners 130A, 130B includes (i) a third button 130A' operatively connected to the multi-ply member 20 and being selectively, disengageably fastenable with the third elastomeric member 110 through apertures among the first sub-plurality of apertures 120A', 120W, 120C', 120D' and (ii) a fourth button 130W operatively connected to the multi-ply member 20 and being selectively, disengageably fastenable with the third elastomeric member 110 through apertures among the second sub-plurality of apertures 120E', 120F' 120G', 120H'. It is to be appreciated that any fastening area among the third plurality of fastening areas 120A, 120B, 120C, 120D, 120E, 120F, 120G, 120H can alternatively be positioned at any area where the third elastomeric member 110 is adapted to be selectively and disengageably fastenenable with any among the fifth plurality of fasteners 130A, 130B and that the third plurality of fastening areas 120A, 120B, 120C, 120D, 120E, 120F, 120G, 120H and fifth plurality of fasteners 130A, 130B may alternatively be formed by other selectively mateable fastening assemblies including, without limitation, mateable hooks and piles, mateable hooks and latches or mateable hooks and loops.

In a preferred embodiment of the diaper 10 perhaps best seen in FIGS. 3 and 4: (1) the third elastomeric member 110 is operatively connected to the multi-ply member 20 through a channel 20K' formed between an elongate retaining piece 20K and an upper segment 20L of the first curvilinear portion 20A of the multi-ply member 20, the elongate retaining piece 20K being operatively connected to the multi-ply member by a third thread segment 160C' stitched through the first curvilinear portion 20A and the elongate retaining piece 20K and (2) the third elastomeric member 110 is further secured to the multi-ply member 20 at a third permanent connection area 160C preferably formed by a third thread segment 160C' stitched through the third elastomeric member 110 and the multi-ply member 20. In a preferred embodiment, an elongate protection member 20M is operatively connected and disposed interiorly to the first curvilinear portion 20A to provide: (a) added comfort to the diaper wearer and (b) added protection and durability to the retaining piece 20K and the third elastomeric member 110.

The features described in the preceding two paragraphs function inter alia to provide a reusable adjustable diaper 10 forming a comfortable yet snug, secure, waste-retaining fit around an unlimited number of differing waist 180C sizes of the diaper wearer including any waist with a circumference: (a) equal to or greater than a minimum sum distance H (FIG. 8) of (1) a third minimum distance F from the third permanent connection area 160C to a fastening area among the first sub-plurality of fastening areas 120A, 120B, 120C, 120D most proximate the third permanent connection area 160C when the third elastomeric member 110 is in a constricted configuration 110' (FIG. 8) and (2) a fourth minimum distance G (FIG. 8) from the third permanent connection area 160C to a fastening area among the second sub-plurality of fastening areas 120E, 120F, 120G, 120H most proximate the third permanent connection area 160C when the third elastomeric member 110 is in a constricted configuration 110' and (b) equal to or less than a maximum sum distance H' (FIG. 8) of (1) a third maximum distance F' (FIG. 8) from the third permanent connection area 160C to a fastening area among the first sub-plurality of fastening areas 120A, 120B, 120C, 120D most distal the third permanent connection area 160C when the third elastomeric member 110 is fully stretched and (2) a fourth maximum distance G' (FIG. 8) from the third permanent connection area 160C to a fastening area among the second sub-plurality of fastening areas 120E, 120F, 120G, 120H most distal the third permanent connection area 160C when the third elastomeric member 110 is fully stretched.

In a preferred embodiment of the reusable pad assembly 20F principally seen in FIGS. 3, 4, 5, and 6: (1) the jacket 20F' is elongate, curvilinear and includes a first jacket ply 200 operatively connected proximate a first jacket end 20P and proximate a second jacket end 20Q to a second jacket ply 20R such that a plurality of elongate jacket slits 20S' 20S" are formed and disposed through the jacket 20F'; and (2) each insert 20F" is elongate, curvilinear and includes a first insert ply 20T operatively connected proximate a first insert end 20U and proximate a second insert end 20V to a second insert ply 20W such that a plurality of elongate insert slits 20X', 20X" are formed in the insert 20F". In standard usage of a preferred embodiment, the insert 20F is removably inserted through a jacket slit among the plurality of jacket slits 20S' 20S" into a void 20Y formed between the first jacket ply 200 and the second jacket ply 20R.

The elongate insert slits 20X', 20X" (FIGS. 5 and 6) facilitate easy placement and selective retention of one insert 20F''' in another and allow easier access to an interior surface 20T' of the first insert ply 20T and an interior surface 20W' the second insert ply 20W after diaper usage to facilitate easier, more rapid washing and drying and the more complete cleaning of each insert 20F". The elongate jacket slits 20S' 20S" also facilitate easy placement and selective retention of one or more inserts 20F" in the jacket 20F' and allow easier access to an interior surface 20O' of the first jacket ply 20O and an interior surface 20R' the second jacket ply 20R after diaper usage to facilitate easier, more rapid washing and drying and the more complete cleaning of the jacket 20F'. The insert 20F" is preferably composed of water absorbing materials, most preferably cotton, hemp, bamboo and blends thereof to facilitate capture of excreted waste therein. The jacket 20F' is preferably composed of a material that dries faster than the insert 20F", most preferably microfiber fleece.

In a preferred embodiment, the composition and structure of the inner ply 20", the outer ply 20' and the reusable pad assembly 20F (a) facilitate easy cleaning and drying after use by a common household washing machine and dryer and (b) facilitate selection from among varying degrees of absorbency to meet changing waste capture needs by allowing selective insertion of the jacket 20F' between the outer ply 20' and the inner ply 20" and the further selective insertion of one or more inserts 20F' within the jacket 20F'. The foregoing is considered as illustrative only of the principles of the invention. Since modifications and changes will occur to those skilled in the art, it is not desired to limit the invention to the exact construction and operation shown and described, and, accordingly, all suitable modifications and equivalents may be resorted to, falling within the scope of the invention. The materials used in construction of the apparatus include polymers and fabrics which provide strength, durability, comfort and ease of use and cleaning.

What is claimed is:

1. A reusable adjustable diaper comprising:
a multi-ply member having a first curvilinear portion connected by a narrowing curved medial portion to a second curvilinear portion;
a first elastomeric member operatively connected along a first curved segment of said medial portion, said first elastomeric member having a first plurality of fastening areas disposed therewith;
a second elastomeric member operatively connected along a second curved segment of said medial portion, said second elastomeric member having a second plurality of fastening areas disposed therewith;
a first plurality of fasteners operatively connected to said first curvilinear portion;
a second plurality of fasteners operatively connected to said second curvilinear portion and being disengagably fastenable with said first plurality of fasteners;
a third fastener operatively connected to said multi-ply member and being disengagably fastenable with said first elastomeric member at said first plurality of fastening areas;
a fourth fastener operatively connected to said multi-ply member and being disengagably fastenable with said second elastomeric member at said second plurality of fastening areas;
a third elastomeric member operatively connected to said first curvilinear portion said third elastomeric member having a third plurality of fastening areas disposed therewith; and a fifth plurality of fasteners operatively connected to said first curvilinear portion and being disengageably fastenable with said third elastomeric member at said third plurality of fastening areas.

2. A reusable adjustable diaper as in claim 1 wherein:
said first plurality of fastening areas comprise a first plurality of uniformly sized and spaced apart apertures disposed through said first elastomeric member;
said second plurality of fastening areas comprise a second plurality of uniformly sized and spaced apart apertures disposed through said second elastomeric member;
said third fastener comprises a first button that is selectively and disengageably fastenable with said first elastomeric member through said first plurality of uniformly sized and spaced apart apertures; and
said fourth fastener comprises a second button that is selectively and disengageably fastenable with said second elastomeric member through said second plurality of uniformly sized and spaced apart apertures.

3. A reusable adjustable diaper as in claim 1 wherein:
said third plurality of fastening areas includes:
a first sub-plurality of uniformly sized and spaced apart apertures disposed through said third elastomeric member;
a second sub-plurality of uniformly sized and spaced apart apertures disposed through said third elastomeric member;
said fifth plurality of fasteners includes:
a third button selectively and disengageably fastenable with said third elastomeric member through said first sub-plurality of fastening areas; and
a fourth button selectively and disengageably fastenable with said third elastomeric member through said second sub-plurality of fastening areas.

4. A reusable adjustable diaper as in claim 1 wherein said first plurality of fasteners and said second plurality of fasteners comprise mateable snap assemblies.

5. A reusable adjustable diaper as in claim 1 wherein said multi-ply member comprises:
an outer ply having a first outer ply curvilinear portion connected by a narrowing curved outer ply medial portion to an outer ply second curvilinear portion;
an inner ply having a first inner ply curvilinear portion connected by a narrowing curved inner ply medial portion to an inner ply second curvilinear portion said inner ply being operatively connected to said outer ply; and
a reusable pad assembly removably inserted through an insertion aperture into a cavity formed between said outer ply and said inner ply.

6. A reusable adjustable diaper as in claim 5 wherein said reusable pad assembly comprises:
a jacket including a first jacket operatively connected to a second jacket ply, a jacket slit being disposed through said jacket;
an insert including a first insert ply operatively connected to a second insert ply, an insert slit being disposed through said insert; and
wherein said insert is removably inserted through said jacket slit into a void formed between said first jacket ply and said second jacket ply.

7. A reusable adjustable diaper as in claim 6 wherein said jacket is composed of a material selected from among a group consisting of cotton, hemp and bamboo.

8. A reusable adjustable diaper as in claim 5 wherein said inner ply is water permeable said outer ply is water impermeable.

9. A reusable adjustable diaper as in claim 5 wherein said insertion aperture comprises an incurvate opening area and said multi-ply member includes a grip tab area disposed peripherally to said incurvate opening area.

10. A reusable adjustable diaper as in claim 5 wherein a fourth elastomeric member is operatively connected to said inner ply proximate said insertion aperture.

11. A reusable adjustable diaper comprising:
   leg openings each having fasteners connected thereto;
   a crotch portion, connected to the leg openings, the crotch portion having fastener reception portions disposed thereon; and
   at least one leg elastic, having an adjustable length, to elasticize each said leg opening, the at least one leg elastic being connected along a curved segment of the crotch portion, wherein:
      each said fastener reception portion is connectable to a corresponding said fastener; and
      the size of the opening of each said leg opening is adjustable by adjusting:
         the fasteners on the leg opening; and
         the adjustable length of the at least one leg elastic.

12. The reusable adjustable diaper as defined in claim 11 wherein each said fastener comprises a mateable snap assembly.

13. A reusable adjustable diaper comprising:
   a pair of multi-ply curvilinear portions each having fasteners disposed thereon;
   a pair of curved medial portions each having fastener reception portions dispose thereon; and
   an elastomeric member, having an adjustable length, connected along a curved segment of each said curved medial portion, wherein:
      when some said fastener reception portions are connected to some said fasteners two leg openings are defined by:
         the pair of multi-ply curvilinear portions;
         the pair of curved medial portions; and
         the elastomeric member; and
      the size of each said leg opening is adjustable by adjusting:
         the fastener reception portions that are connected to the fasteners; and
         the adjustable length of the elastomeric member.

14. The reusable adjustable diaper as defined in claim 13, wherein:
   each said elastomeric members elasticizes a corresponding said multi-ply curvilinear portion; and
   the fasteners are connected to each said multi-ply curvilinear portion, whereby the girth of each said multi-ply curvilinear portion can be adjusted by selectively fastening or unfastening each said fastener from a corresponding said fastener reception portion.

15. The reusable adjustable diaper as defined in claim 13, wherein each said multi-ply curvilinear portion comprises:
   an outer ply having a first outer ply curvilinear portion connected by a narrowing curved outer ply medial portion to an outer ply second curvilinear portion;
   an inner ply having a first inner ply curvilinear portion connected by a narrowing curved inner ply medial portion to an inner ply second curvilinear portion said inner ply being operatively connected to said outer ply; and
   a reusable pad assembly removably inserted through an insertion aperture into a cavity formed between said outer ply and said inner ply.

16. The reusable adjustable diaper as defined in claim 15, wherein said inner ply is water permeable said outer ply is water impermeable.

17. The reusable adjustable diaper as defined in claim 15, wherein:
   said insertion aperture comprises an incurvate opening area; and
   said multi-ply member includes a grip tab area disposed peripherally to said incurvate opening area.

18. The reusable adjustable diaper as defined in claim 15, wherein said reusable pad assembly comprises:
   a jacket including a first jacket ply operatively connected to a second jacket ply, a jacket slit being disposed through said jacket;
   an insert including a first insert ply operatively connected to a second insert ply, an insert slit being disposed through said insert; and
   wherein said insert is removably inserted through said jacket slit into a void formed between said first jacket ply and said second jacket ply.

19. The reusable adjustable diaper as defined in claim 13, wherein each said fastener comprises a mateable snap assembly.

20. The reusable adjustable diaper as defined claim 18, wherein said jacket is composed of a material selected from among a group consisting of cotton, hemp and bamboo.

* * * * *